(12) United States Patent
Levinson

(10) Patent No.: US 7,871,385 B2
(45) Date of Patent: Jan. 18, 2011

(54) URINE SAMPLE COLLECTION DEVICE

(76) Inventor: Orde Levinson, Caudwell's Castle, Folly Bridge, Oxford (GB) OX1 4LB ( * ) Notice: Subject to any disclaimer, the term of this patent is extended or adjusted under 35 U.S.C. 154(b) by 0 days.

(21) Appl. No.: 12/423,348

(22) Filed: Apr. 14, 2009

(65) Prior Publication Data

US 2009/0259205 A1  Oct. 15, 2009

Related U.S. Application Data

(63) Continuation of application No. 10/505,232, filed as application No. PCT/GB03/00472 on Feb. 4, 2003, now abandoned.

(30) Foreign Application Priority Data

Feb. 20, 2002 (GB) .................................. 0203993.1
Apr. 18, 2002 (GB) .................................. 0208895.3
Jun. 13, 2002 (GB) .................................. 0213601.8

(51) Int. Cl.
*A61B 5/00* (2006.01)
*B65D 81/00* (2006.01)
(52) U.S. Cl. ..................................................... 600/573
(58) Field of Classification Search ................ 4/144.1, 4/144.2, 144.3, 144.4; 600/573, 574, 579
See application file for complete search history.

(56) References Cited

U.S. PATENT DOCUMENTS

| 3,161,891 A | | 12/1964 | Bauman |
| 3,750,647 A | | 8/1973 | Gleason et al. |
| 4,252,132 A | * | 2/1981 | Kuntz .......................... 600/574 |
| 4,494,581 A | | 1/1985 | Gordon |

FOREIGN PATENT DOCUMENTS

| WO | 9013280 | 11/1990 |
| WO | 0174275 A1 | 10/2001 |

* cited by examiner

*Primary Examiner*—Max Hindenburg
*Assistant Examiner*—Jonathan M. Foreman

(57) ABSTRACT

A urine sample collection device comprising a urine receptor having an outlet aperture, a generally elongate tubular member extending from said receptor outlet aperture to an open end, the tubular member having an opening (21) formed in the side thereof, a coupling means (5') for releasably mounting a urine collection container, the coupling means having a passage extending therethrough which meets said opening whereby urine can flow from the tubular member into a mounted container, and a flow director (24) located at or adjacent said opening and formed to direct urine past the opening.

12 Claims, 3 Drawing Sheets

URINE SAMPLE COLLECTION DEVICE

CROSS REFERENCE TO PRIOR APPLICATION

This application is a continuation of application Ser. No. 10/505,232 filed Apr. 18, 2005.

The present invention relates to a urine sample collection device.

The Applicant is the proprietor of earlier patent application WO-A-01/74275, now U.S. Pat. No. 7,435,242. this application details the various reasons why urine samples are collected, and the uses for the results of the analysis of the collected sample.

FIG. 1 illustrates a urine sample collection device 1 based on the disclosure of this earlier patent application. The device has a urine receptor generally identified by reference numeral 2. This comprises a surface 7 which defines at one end an outlet aperture 3 and which flares out to define at its other end a rim 8 forming a perimeter of an inlet area into which a user urinates. The various forms of the receptor are described in more detail in the aforementioned patent application. The outlet aperture is coupled to one end of a generally elongate hollow tubular member or pipe portion 4. The other end of the tubular member is open. The tubular member 4 narrows along its length and the end remote from the outlet aperture 3 defines a generally oblong excess outlet aperture 6. A sample container coupling 5 comprises a short hollow stub like tube which is formed with a passage therethrough which meets an opening in the centre of the side of the tubular member. The sample container coupling 5 is located along the tubular member 4 to be spaced from the outlet aperture 3. The sample container coupling is formed to provide a push fit for a standard urine sample collection container or bottle (not shown). The sample container coupling 5 is located and formed such that the sample container is orientated vertically downwards during use.

In use, a standard tubular urine sample collection container (not shown) is pushed onto the sample container coupling 5. A female user then locates the receptor 2 against their body to cover the urethra as explained more fully in the aforementioned patent application. A male user locates the end of their penis into the receptor.

The user then urinates and urine flows along the tubular member and flows both into the urine sample collection container and out of the excess outlet aperture 6. Once the collection container is full, the user can simply finish urinating because excess urine flows out of the excess outlet 6. Alternatively, the user can withdraw the device 1 and continue to urinate, but this increases the likelihood of contamination to their hands.

In this type of device, the urine flows through the device and out of the excess outlet aperture with a proportion of that urine flow being collected in the collection container via sample container coupling 5. This through flow type of device differs from devices where all the urine flow is directed straight into a collection container.

However, filling the urine collection container to capacity can cause problems. For example, uncoupling the full collection container from the collection device without spillage may be problematic.

It is an object of the present invention to provide an improved urine sample collection device. According to the present invention there is provided a urine sample collection device comprising:

a urine receptor having a surface which flares out from an outlet aperture to a rim defining a perimeter of an inlet area into which a user urinates;

a generally elongate tubular member extending from said receptor outlet aperture to an open end, the tubular member having an opening formed in the side thereof;

a coupling means for releasably mounting a urine collection container, the coupling means having a passage extending therethrough which meets said opening whereby urine can flow from the tubular member into a mounted container; and a flow director located at or adjacent said opening and formed to direct urine past the opening.

A view has been expressed by medical personnel that it is important to sample the urine mid stream. One justification for obtaining a mid stream urine (MSU) sample is that if there is any initial contamination in or around the urinary tract or urethra, such contamination will be flushed out at the start of urination. Another justification is that a MSU sample is more representative of the contents of the bladder than that at the start of urination and is less dependent on personal hygiene.

In this case, if an MSU sample is to be obtained, it is important not to collect the initial flow at the start of urination and immediately thereafter. Unfortunately, with the device shown in FIG. 1, it is not possible to guarantee that a proportion of this initial flow will not be collected. The flow director of the present invention can be used to direct urine which is not from the midstream towards the open end of the tubular member and direct midstream urine into the urine collection container.

It should be noted that by flared out we mean any shape which changes from a narrow shape to a broad shape.

Preferably the flow director comprises a projection towards the axis of the tubular member.

In one embodiment, the projection is provided upstream of the opening. This projection can be used to divert the flow of the urine away from the opening.

In another embodiment, the projection is also formed downstream of the opening.

In one preferred embodiment, the projection upstream of the opening has an inclined surface.

In another preferred embodiment, the projection upstream of the opening comprises a wall which extends across the tubular member to an extent corresponding to the upstream edge of said opening.

Conveniently, the flow director is formed to channel the urine flow along either side of the aperture.

In a preferred embodiment of the present invention, the projection towards the axis of the tubular member may comprise a passage of the coupling means, the passage extending into the tubular member and presenting an area within the tubular member into which urine can enter and flow into the collection container. The area does not have to be in the same plane as the walls of the elongate tubular member.

Preferably, the passage of the coupling means extends into the tubular member by an amount corresponding to between 20 and 60% of the height of the tubular member. The area conveniently comprises a semi-circle, and the extension of the passage into the tubular member is greater downstream than upstream.

The coupling means preferably includes a further passage extending therethrough which meets said opening to present an area from which air in the collection container can escape into the tubular member. The further passage of the coupling means preferably extends into the tubular member by an amount which is greater than the urine passage.

The further (air) passage can be upstream or downstream of the urine passage. It should be noted that by designating the passages air and urine it does not preclude other fluids or a mixture thereof flowing through the passages (e.g air can flow through the urine passage).

Preferably an opening of the further passage in the tubular member faces downstream.

In a preferred embodiment the opening in the further passage is at an incline facing downstream.

Conveniently, in addition or in the alternative, a covering means is provided adjacent the opening in the further passage.

The body has evolved such that urine traveling out of the body travels in a spiral configuration in order to reduce the amount spraying. As the urine travels down the elongate tubular member in a spiral configuration it can cause an air lock in the further passage. As will be appreciated, the air lock stops the urine flowing into the urine collection container. If the opening of the passage faces downstream, is at an incline or there is a cover provided to deflect the urine away from the opening then the likelihood of an air lock being produced is reduced.

It is preferred that the tubular member tapers to a smaller cross-section at said open end. Accordingly, the urine which is flowing through the tubular member and past the opening in the side thereof will begin to "back-up" when sufficient urine is flowing (i.e during the midstream) and, therefore, will start to flow through the opening in the side of the tubular member and into the urine collection container.

Preferably the device further comprises a flow limiter, or urine collection container having a flow limiter, for limiting flow of urine into the container.

The flow limiter preferably allows urine to enter a container to a predetermined limit, after which further urine is prevented from entering the container. In this way, the amount of urine entering the container cannot exceed a predetermined maximum, for example beyond a fraction (e.g. from 50 to 75%) of the capacity of the container.

The flow limiter may limit flow of urine into the container by preventing ingress of urine, or by preventing egress of displaced air from the container. For example, the flow limiter may prevent ingress of urine into the container by means of a valve between the opening and a container in use, which valve closes when the urine in the container reaches a predetermined level. Alternatively, the device may comprise a passage, for example between the container and the tubular member, through which air displaced from the container by ingress of urine can escape from the container, whereby urine is prevented from entering the container by the urine level rising to cover the container-side opening of the passage. In this way, further urine is prevented from entering the container by preventing air from being displaced from the container.

In the present invention the urine and air passages extend into the container, which is fitted to the device such that substantially all fluid transfer between the tubular member and the container occurs via the said passages, in particular transfer of urine from the tubular member to the container via the urine passage and transfer of air from the container to the tubular member via the air passage. Thus, as urine enters the container via the urine passage air is displaced into the tubular member via the air passage. However, when the level of urine in the container rises to cover the container-side opening of the air passage, no further air can be displaced from the container into the tubular member, and hence no further urine can enter the container. The amount of urine which can enter the container is thus largely determined in this embodiment by the extent to which the second passage extends into the container.

In another preferred embodiment of the present invention, the flow limiter comprises a valve through which urine can flow from the tubular member into a container. For example, the valve may comprise a lower opening through which urine can pass into the container, an upper opening through which urine can enter the valve from the tubular member, and a closure member positioned between the upper and lower openings, and dimensioned so as to be capable of closing the upper opening. In this embodiment, the closure member may conveniently have a density lower than that of urine, i.e. it will float in urine, so that as the level of urine in the container rises to reach the closure member it will float upon the urine. Thus, the closure member will rise with the urine, until it reaches the upper opening to form a seal therewith, thus preventing further urine from entering the container. Once the upper opening has been sealed in this way, as the user continues to urinate, further urine will merely pass through the tubular member from the device.

Examples of the invention will now be described with reference to the following figures, in which.

Figure 1:
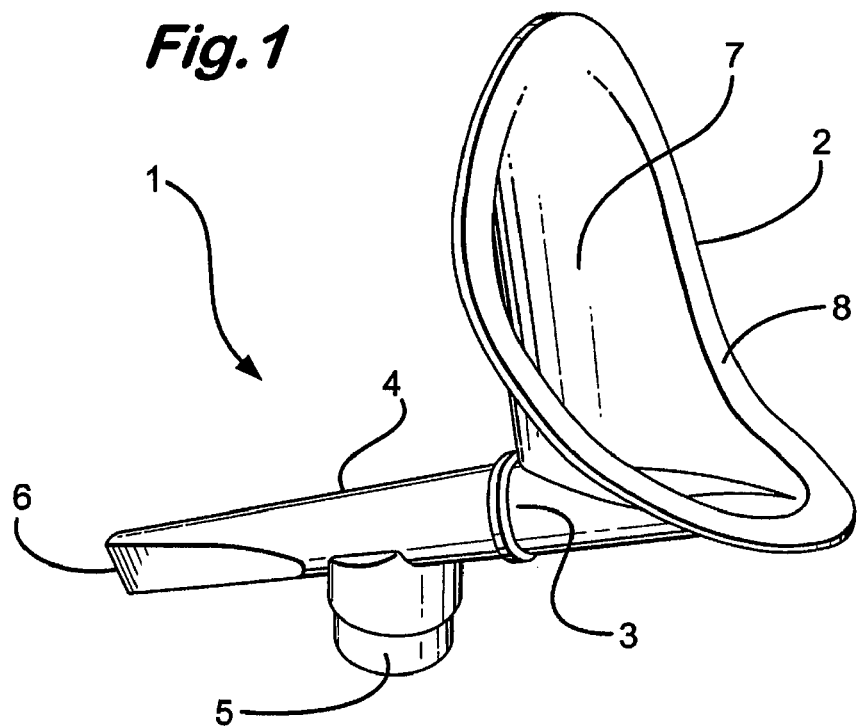
FIG. 1 shows an oblique perspective view of a known urine sample collection device.

Component parts which are common amongst the figures bear common reference numerals.

It is considered that if a through flow type of device as shown in FIG. 1 is to obtain a mid stream urine sample, it is necessary to ensure that as little as possible of the initial urine flows into the collection container. It is considered that the proportion of urine entering the collection container, at least during the initial flow, will be a function of the area of the opening to the passage through the sample container coupling 5, that is to say, the opening of the passage onto the tubular portion 4, and the velocity (and hence momentum) of the urine flow upstream of the coupling. The former can be designed whilst the latter will be influenced by the bladder of the user and by gravity consequent to the angle of the urine flow in the tubular portion relative to vertical.

One option to reduce the proportion of urine entering the collection container during the initial flow would be to make the aforementioned area smaller and/or increase the velocity of the urine flow. Unfortunately, this tends to lead to problems with the overall urine collection to the point that the collection container remains substantially empty.

Figure 2:
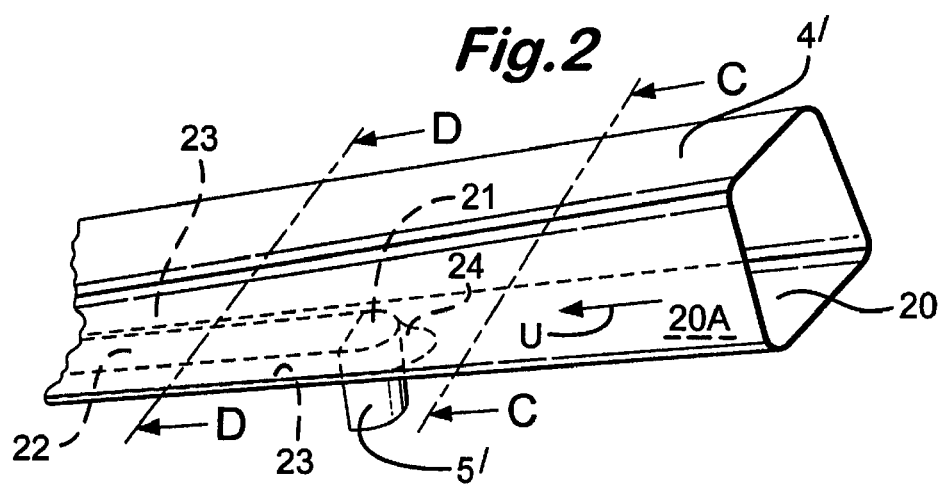
FIG. 2 shows a perspective side view of a tubular member part of an embodiment of the present invention.
Figure 3:
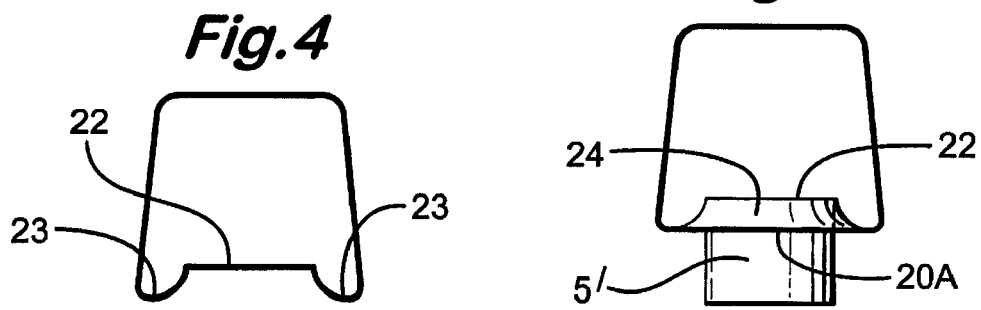
FIG. 3 shows the cross-sectional views along the line C-C of FIG. 2.
Figure 4:
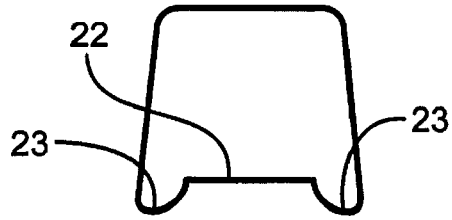
FIG. 4 shows the cross-section along the line D-D of FIG. 2.

FIG. 2 illustrates an oblique perspective view of a portion of a tubular member 4' corresponding to the tubular member 4 shown in FIG. 1. The precise form of the receptor is not material to the present invention. In this embodiment, the tubular member has a generally square cross section as shown in the drawings but is not limited thereto. The tubular member has a base 20 from which a sample container coupling 5' extends. The sample container coupling 5' has a passage therethrough which meets an opening formed in the base of the tubular member 4', the opening defining a planar area 21. Thus, urine flowing down the tubular member 4' can pass down into a collection container (not shown) fitted to the coupling 5'. The flow of urine in the tubular member 4' is indicated by an arrow U, substantially along the axis of the tubular member.

In this embodiment, the base 20A which is upstream of the area 21 is formed to include an inclined surface or ramp 24 which leads up to the area 21. The ramp therefore projects towards the axis of the tubular member. The area 21 is substantially parallel to the surface of upstream base 20A but is not in the same plane. Downstream of the area 21, the central member of the base of the tubular member 4' along the axis thereof defines a plateau surface 22 which is on the plane defined by the area 21. Towards either edge of this plateau surface, channels 23 are formed which extend either side of the area 21 to meet the base 20 which is upstream of the area 21. The base of the channels 23 is on the plane of the base 20 which is upstream of the area 21.

Thus, when urination starts, if the urine is flowing slowly, urine will flow along the channels 23 and pass either side of the area 21 so that none of this initial flow will pass into the collection container through the area 21. As the urine flow builds up in velocity, it will tend to rise up the ramp 24. Eventually, the urine will tend to travel entirely up the ramp and will be directed over the area 21. However, due to the velocity, the urine will tend not to fall onto the area but instead pass completely over it so that none of this flow will pass into the collection container through the area 21. Consequently, the channels and ramp 24 function to direct the flow of urine past the area 21.

Generally speaking, the volume of urine entering the tubular member 4' will eventually be greater than that leaving through the aperture 6. Thus, a front of fluid begins to "back up" along the tubular member. When the front reaches the area 21, the collection container will begin to fill. Thus, the early part of the urine flow does not pass into the collection container so that an MSU sample is collected.

Consequently, by having a ramp 24 to direct the urine to pass over the area 21 facilitates the collection of an MSU sample. In addition, by having the channels 23, if the initial urine flow is very slow, for example due to urological diseases or infections which can cause pain or for those with voiding difficulties or obstructions, this slow moving urine is directed either side of the area 21 and is not collected. In addition, in cases where imperfect personal hygiene tends to contaminate the early part of a urine sample, this contaminated part of the urine flow is not collected.

The present invention is capable of considerable modification, the detailed embodiments of which will be readily apparent to those skilled in the art. For example, whilst the present embodiment has been described to include channels 23, these can be omitted such that the ramp 24 extends across the width of the base 20 if very slow urine flow is not to be considered a problem during urine collection. It will be appreciated that the angle and size of ramp can be varied. Whilst a ramp has been described as the flow director, a wall can be used which extends across the base 24 to an extent corresponding to the upstream edge of the area 21 such that the area is masked from the direct flow of urine along the tubular member 4'. The wall can also be V-shaped pointing upstream so that slow moving urine is directed around the area 21. Alternatively, the coupling 5' can be made such that it extends through the base 20 whereby its upper edge defines the area 21 which is in a plane located displaced relative to the base 20.

Figure 5:
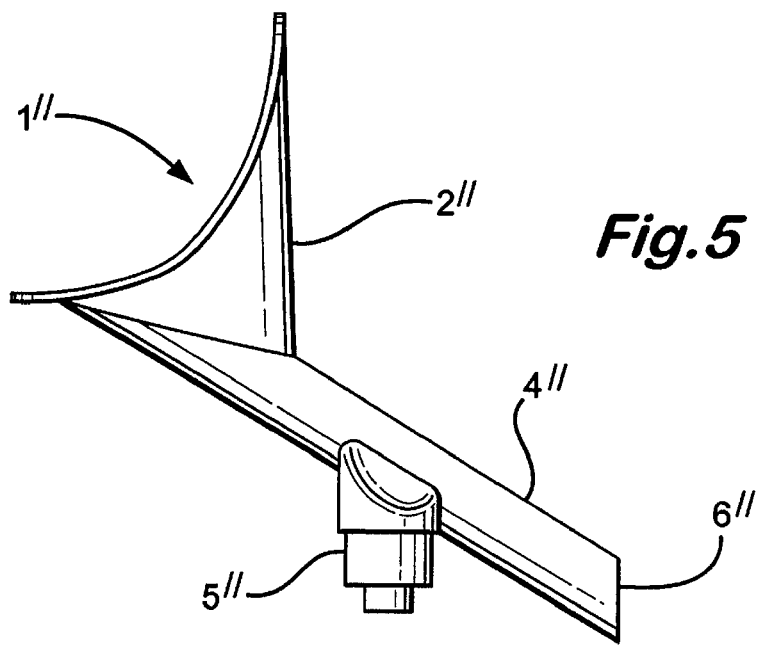
FIG. 5 illustrates a side view of a receptor, tubular member and coupling means parts of another embodiment of the present invention.
Figure 6:
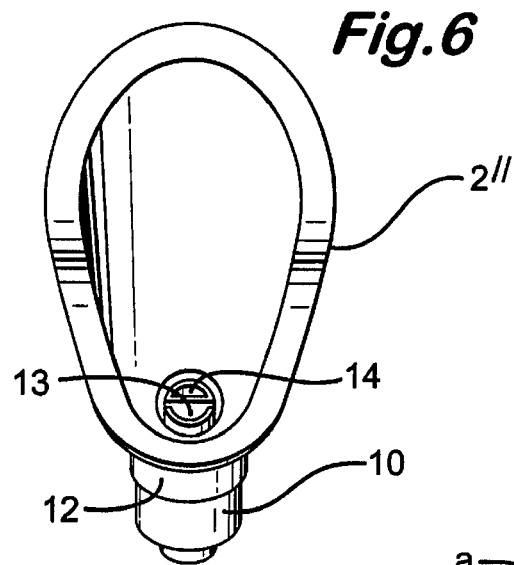
FIG. 6 illustrates a plan view of the urine receiving portion of FIG. 5 as viewed along the axis of the tubular member.
Figure 7:
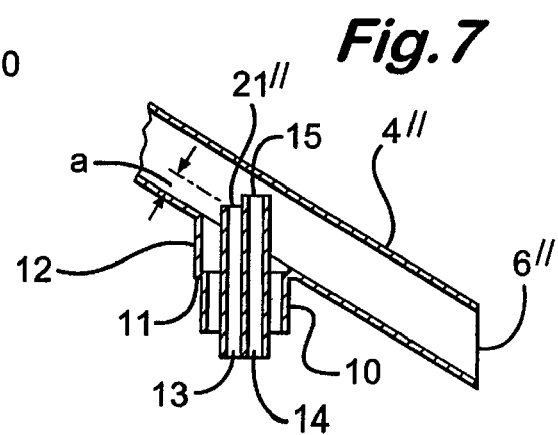
FIG. 7 illustrates a cross-sectional side view taken along the length of the tubular member part of FIG. 5 omitting the urine receptor.

In this respect, referring to the urine sample collection device 1" shown in FIGS. 5 to 7, the urine receptor 2" is substantially identical to that shown in FIGS. 1 to 4. However, it will be noted that the device has a tubular member 4" which comprises a constant circular cross-section tube, that is to say, it does not narrow between the urine receptor 2" and the excess outlet aperture 6".

A sample container coupling 5" is located as with FIGS. 1 to 4. As can be seen from FIGS. 6 and 7, the outer surface of the coupling 5" has a portion 10 at the end onto which a sample container can be attached, this portion having a circular cross-section outer surface. The outer surface of the coupling 5" also has a portion 12 where the coupling meets the tubular member 4". The portion 12 has a larger circumference than the portion 10, the portions 10 and 12 meeting at an elbow 11.

A passage is formed through the coupling 5" which comprises a circular cross-section tube which is split into first and second separate channels 13 and 14 having respective semi-circular cross-sections, as can be seen from FIG. 6. One end (the lower end) of the channels 13 and 14 extend equally from the lower edge of the portion 10, as can be seen from FIG. 7. The other end (the upper end) of the channels 13 and 14 extend through the base of and into the tubular member 4". The upper edge of the channel 14 extends further into the tubular member 4" than the channel 13 and is located on the side towards the outlet aperture 6" (downstream). The upper edge of the channel 13 defines a semi-circular area 21" whilst the upper edge of the channel 14 defines a semi-circular area 15.

When urination starts, if the urine is flowing slowly, urine will flow down the tubular member 4" and will flow either side of the channels 13 and 14 extending into the member 4". Thus, none of this initial flow will pass into a collection container. As the urine flow builds up in velocity, the flow in the tubular member 4" will become deeper until the depth reaches a value of "a", which comprises the distance (the height) of the upstream edge of the channel 13 from the base of the tubular member 4", as shown in FIG. 7. At this point, urine will start to flow into the area 21" and down through the channel 13 into the collection container. The downstream channel 14 acts as an air vent for air to escape from the collection container as it fills. The upper edge 15 has a height from the base of the tubular member 4" which is greater than "a" so that urine does not normally flow down channel 14. The height "a" is preferably in the range of 20 to 60% of the height of the tubular member 4" at the point of the coupling 5". In this case, the tubular member has a diameter "d" and hence a=20-60% of d. Thus, the area 21" is effectively spaced from the base or lower surface of the tubular member 4" by an a distance which provides a wall against slow flowing urine.

It will be apparent that an air vent for the collection container can be provided in a different manner.

The present invention may be produced from a plastics material injected into a tool having a shaped insert to form the tubular member 4'. In the described embodiment of FIGS. 2 to 4, the tubular insert can be a single piece that is withdrawn in the direction of the receptor 2. If a two piece insert is used, it is possible to have the area 21 made such that it is in the plane of the base 20 but the top edge of the ramp 24 remains displaced from the plane of the base.

By having a construction as shown in the embodiment of FIGS. 5 to 7 and with a tubular member 4" which does not narrow, it is possible to produce a tool in which a shaped insert can form the tubular member 4" by insertion into opposing ends thereof.

Figure 8:
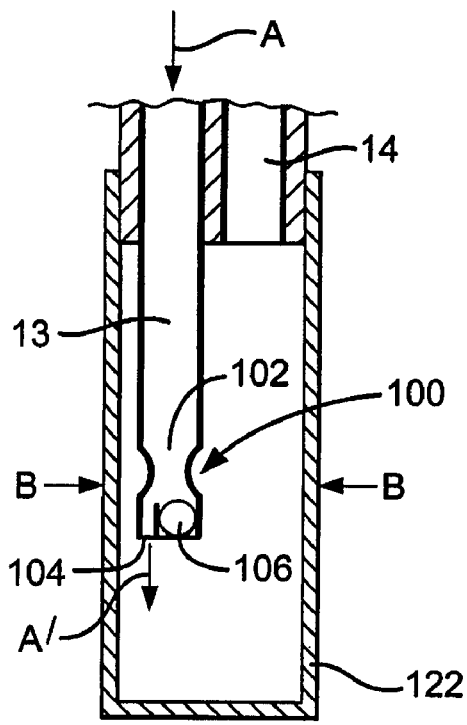
FIG. 8 illustrates a flow limiter for use with the urine sample collection devices shown in the previous Figures.

Referring to FIG. 8, a flow limiter for use with the urine collection devices illustrated in the previous Figures comprises a valve 100 for preventing ingress of urine into a container 122. The valve 100 is positioned within the first channel 13, described with reference to FIGS. 5 to 7, with corresponding second channel 14 for escape of displaced air into the tubular member (not shown in FIG. 8). The valve 100 comprises an upper opening 102, a lower opening 104 and a closure member in the form of a ball 106. The ball 106 has an overall density lower than that of urine, and will thus float on urine, and is initially maintained in position away from the lower opening 104 by an internal wall 108 so as not to block the lower opening 104. The diameter of the ball 106 is greater than that of the upper opening 102. In use, urine will enter the valve 100 from the tubular member as indicated by arrow A, passing through and out of the valve 100 as indicated by arrow A' into the container 122. The urine level in the container 122 will rise, and after a time will enter the valve 100 via lower opening 104. As the urine level continues to rise within the valve 100, the ball 106 will float on the urine, until it reaches the upper opening 102, i.e. urine will rise within the container 122 to the level approximately indicated by arrows B in FIG. 8. The ball 106 will then close the upper opening 102, thus preventing further urine from entering the valve 100, and hence the container 122. As the user continues to urinate, further urine cannot pass through the valve 100 into the container 122, but merely passes through and from the tubular member. Of course, urine will be present within the first channel 13 above the valve 100 between the tubular member and the valve 100, which urine will drop into the container 122 when the ball 106 drops from the upper opening 102 as the container 122 is removed from the device. The total amount of urine to be collected can thus be predetermined from the position of the valve 100 within the container 122 in use, and the capacity of the first channel 13 between the tubular member and the valve 100. Urine spillage on removal of the container 122 from the device can be substantially prevented by ensuring that the capacity of the container 122 above the level of the valve 100 in use is greater than the capacity of the first channel 13 between the tubular member and the valve 100.

Figure 9:
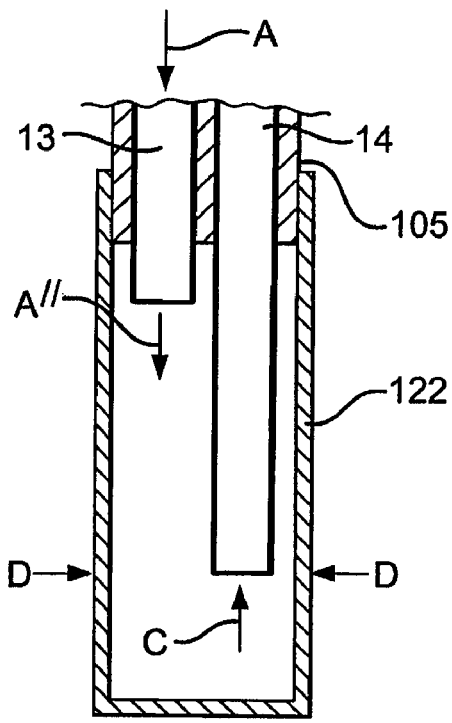
FIG. 9 illustrates a further flow limiter for use with the urine sample collection devices shown in FIGS. 1 to 7.

Referring to FIG. 9, a further flow limiter is illustrated which comprises first and second channels 13 and 14, described with reference to FIGS. 5 to 7. The second channel 14 extends into the container 122 by an amount which is greater than the first channel 13. The container 122 forms a fluid tight seal with the coupling 105, i.e. urine can enter the container 122 only through first channel 13 and displaced air can only escape from the container 122 through second channel 14. Thus, as described hereinabove with reference to FIGS. 5 to 7, in use urine passes into the container 122 from the tubular member (not shown in FIG. 9) via channel 13, as indicated by arrow A", and displaced air passes out of the container 122 via channel 14, as indicated by arrow C. As the urine level within the container 122 rises it will after a time reach the level of the lower opening of channel 14, as approximately indicated in FIG. 9 by arrows D. At this point, no further air can be displaced from the container 120, and hence no further urine can enter the container 120. Thus, all further urine will pass through the tubular member from the urine collection device. Of course, urine will be present within the first channel 13, which urine will drop into the container 122 when it is removed from the device, i.e. when the fluid tight seal between the container 122 and the coupling 105 is broken and air can escape. The total amount of urine to be collected can thus be predetermined from the position of the lower opening of the second channel 14 within the container 122 in use, and the capacity of the first channel 13. Urine spillage on removal of the container 122 from the device can be substantially prevented by ensuring that the capacity of the container 122 above the level of the lower opening of the second channel 14 in use is greater than the capacity of the first channel 13.

Figure 10:
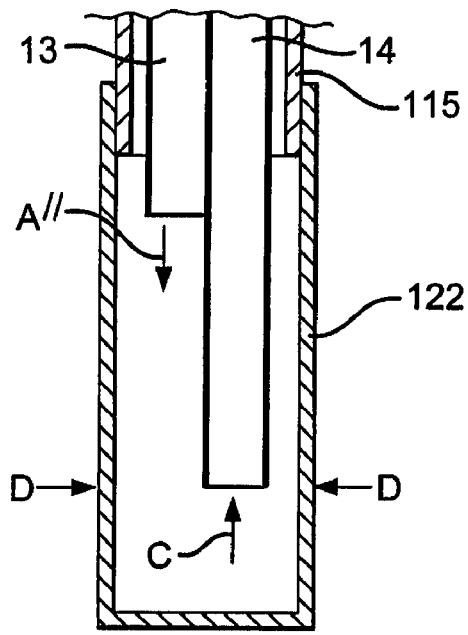
FIG. 10 illustrates a further flow limiter for use with the urine sample collection devices shown in FIGS. 1 to 7.

A further flow limiter for use with the urine sample collection devices shown in FIGS. 1 to 7 is illustrated in FIG. 10. This flow limiter is substantially identical to that shown in FIG. 9 with the exception that the coupling 115 is hollow, and the first and second channels 13 and 14 respectively passing therethrough are contiguous.

It is to be noted that although the flow limiters shown in FIGS. 8, 9 and 10 are described with specific reference to the urine collection device shown in FIGS. 5 to 7, they may be used equally with other urine collection devices, as will be apparent to those skilled in the art.

The invention claimed is:

1. A urine sample collection device, comprising
a urine receptor into which a user urinates;
wherein the urine receptor contains a single outlet aperture flaring out to a rim defining a perimeter of an inlet area into which the user urinates;
a hollow tubular member having a generally elongate form defining a closed tubular chamber, an inlet end containing an inlet opening communicating with said chamber, and an outlet end opposite said inlet end and containing an outlet opening communicating with said chamber;
wherein the tubular member includes an inner surface and a sampling outlet fixture formed in a side wall thereof intermediate the inlet end and the outlet end;
wherein the inlet end of the tubular member is connected with the single outlet aperture of the urine receptor so that all urine from the user flows out of the urine receptor and into the tubular member chamber;
wherein the sampling outlet fixture defines a passage extending through the side wall of the tubular member and communicating with said chamber;
wherein the fixture has an external portion which extends externally out from the tubular member and the external portion contains an external end opening of the passage;
wherein the fixture external portion includes a coupling for releasably mounting an open topped urine sample collection container thereto for collecting urine flowing through the passage and out of the external end opening;
wherein the fixture has an internal portion which extends internally into the tubular member chamber through the side wall of the tubular member and the internal portion contains an internal end opening of the passage; and
a flow diverter formed on the internal portion of the fixture, said flow diverter comprising a surface inclined relative to said inner surface of the closed tubular member to direct smaller urine flows from the urine receptor along the tubular member inner surface past the internal end opening while allowing larger urine flows from the urine receptor within the tubular member to pass through the internal end opening into the passage.

2. A device according to claim 1, wherein said inclined surface extends towards a longitudinal axis of the tubular member.

3. A device according to claim 1, wherein said inclined surface is located upstream of the internal end opening.

4. A device according to claim 3, wherein said inclined surface comprises a wall which extends partially across the tubular member inner surface to an extent corresponding to an upstream edge of said internal end opening.

5. A device according to claim 3, wherein said flow diverter further comprises a projection located downstream of the internal end opening.

6. A device according to claim 1, wherein said flow diverter further comprises a projection shaped to define a channel on one or both sides of the internal end opening.

7. A device according to claim 1, wherein said flow diverter comprises a projection which extends into the tubular member by an amount corresponding to between 20 and 60% of the height of the internal dimension of the tubular member.

8. A device according to claim 1, wherein said fixture internal portion has an internal end opening of the passage which has an area in the form of a semi circle and said flow diverter comprises a projection which extends into the tubular member to a greater extent downstream than upstream.

9. A device according to claim 1, wherein the tubular member tapers to said outlet end.

10. A urine sample collection device, comprising
a urine receptor into which a user urinates;
wherein the urine receptor contains a single outlet aperture flaring out to a rim defining a perimeter of an inlet area into which the user urinates;
a hollow tubular member having a generally elongate form defining a closed tubular chamber, an inlet end containing an inlet opening communicating with said chamber, and an outlet end opposite said inlet end and containing an outlet opening communicating with said chamber;
wherein the tubular member includes an inner surface and a sampling outlet fixture formed in a side wall thereof intermediate the inlet end and the outlet end;
wherein the inlet end of the tubular member is connected with the single outlet aperture of the urine receptor so that all urine from the user flows out of the urine receptor and into the tubular member chamber;
wherein the sampling outlet fixture defines a first passage extending through the side wall of the tubular member and communicating with said chamber;
wherein the fixture has an external portion which extends externally out from the tubular member and the external portion contains an external end opening of the passage;
wherein the fixture external portion includes a coupling for releasably mounting an open topped urine sample collection container thereto for collecting urine flowing through the passage and out of the external end opening;
wherein the fixture has an internal portion which extends internally into the tubular member chamber through the side wall of the tubular member and the internal portion contains an internal end opening of the passage;
wherein the fixture defines a further passage which extends through said external portion to have an external end opening which opens into a mounted urine sample collection container and which extends through said internal portion to have an internal end opening which opens into said tubular member to enable air in the urine sample collection container to pass into the tubular member;
wherein said fixture internal portion is formed so that the internal end opening of the further passage extends into the tubular member further than the internal end opening of the first mentioned passage and wherein said fixture internal portion has an internal end opening of the further passage which faces downstream; and
a flow diverter formed on the internal portion of the fixture, said flow diverter being configured to direct smaller urine flows from the urine receptor along the tubular member inner surface past the internal end opening while allowing larger urine flows from the urine receptor within the tubular member to pass through the internal end opening into the passage.

11. A device according to claim 10, wherein said fixture internal portion has an internal end opening of the further passage which is at an incline facing downstream relative to said inner surface of the tubular member.

12. A device according to claim 10, wherein a covering member is provided adjacent to the opening to the further passage.

* * * * *